(12) United States Patent
Park et al.

(10) Patent No.: US 11,222,653 B2
(45) Date of Patent: Jan. 11, 2022

(54) SYSTEM AND METHOD FOR DETERMINING STROKE BASED ON VOICE ANALYSIS

(71) Applicants: SHINSUNG UNIVERSITY Industry-Academia Cooperation Group, Dangjin-si (KR); Korea Research Institute of Standards and Science, Daejeon (KR)

(72) Inventors: Se Jin Park, Anseong-si (KR); Seung Nam Min, Gwacheon-si (KR); Kyung Sun Lee, Sejong-si (KR); Jung Nam Im, Seoul (KR); Dong Joon Kim, Hwaseong-si (KR); Sung Kyun Im, Seoul (KR); Hea Sol Kim, Osan-si (KR); Murali Subramaniyam, Tamilnadu (IN); Seoung Eun Kim, Asani-si (KR)

(73) Assignees: SHINSUNG UNIVERSITY Industry-Academia Cooperation Group; Korea Research Institute of Standards and Science

( * ) Notice: Subject to any disclaimer, the term of this patent is extended or adjusted under 35 U.S.C. 154(b) by 168 days.

(21) Appl. No.: 16/554,708

(22) Filed: Aug. 29, 2019

(65) Prior Publication Data
US 2020/0118584 A1 Apr. 16, 2020

(51) Int. Cl.
*G10L 25/66* (2013.01)
*G16H 80/00* (2018.01)
(Continued)

(52) U.S. Cl.
CPC ............ *G10L 25/66* (2013.01); *A61B 5/4803* (2013.01); *G06K 9/6278* (2013.01); *G10L 15/02* (2013.01); *G10L 15/22* (2013.01); *G16H 80/00* (2018.01)

(58) Field of Classification Search
None
See application file for complete search history.

(56) References Cited

U.S. PATENT DOCUMENTS

| 10,789,966 B2* | 9/2020 | Honig ................ G10L 25/21 |
| 2007/0179354 A1* | 8/2007 | Stupp ................ G16H 50/70 600/300 |

(Continued)

OTHER PUBLICATIONS

Lee, Seung-Rho, Myoung-Hwan Ko, and Hyun-Gi Kim. "Voice onset time variations of Korean stop consonants in Aphasic speakers." Annals of rehabilitation medicine 35.5 (2011): 694. (Year: 2011).*

(Continued)

*Primary Examiner* — Brian L Albertalli
(74) *Attorney, Agent, or Firm* — Park & Associates IP Law, P.C.

(57) ABSTRACT

The present invention relates to a system and a method for determining a stroke based on a voice analysis. According to the present invention, voice data of subjects are collected to extract and analyze voice onset times to determine stroke patients based on voices. The system for determining a stroke generates and collects voice data from test subjects reading a predetermined word that includes a plosive sound. The system for determining a stroke extracts and calculates voice onset times from the voice data to calculate probability parameters for the voice onset times of each of a normal group and a stroke patient group. The system for determining a stroke uses a set of probability parameters to determine an integration section, and calculates probabilities of being in the normal group and the stroke patient group. The system for determining a stroke applies the calculated probabilities to the Bayes theorem to determine whether the subjects are stroke patients.

6 Claims, 7 Drawing Sheets

(51) Int. Cl.
*A61B 5/00* (2006.01)
*G06K 9/62* (2006.01)
*G10L 15/02* (2006.01)
*G10L 15/22* (2006.01)

(56) References Cited

U.S. PATENT DOCUMENTS

2012/0265024 A1* 10/2012 Shrivastav ............. G16H 50/30
                                                    600/300
2015/0265205 A1*  9/2015 Rosenbek ............ A61B 5/4803
                                                    600/586
2021/0121125 A1*  4/2021 Tokuno ................ A61B 5/4088

OTHER PUBLICATIONS

Özsancak, Canan, et al. "Measurement of voice onset time in dysarthric patients: Methodological considerations." Folia Phoniatrica et Logopaedica 53.1 (2001): 48-57. (Year: 2001).*
Ryalls, Jack, Kristina Gustafson, and Celia Santini. "Preliminary investigation of voice onset time production in persons with dysphagia." Dysphagia 14.3 (1999): 169-175. (Year: 1999).*

* cited by examiner

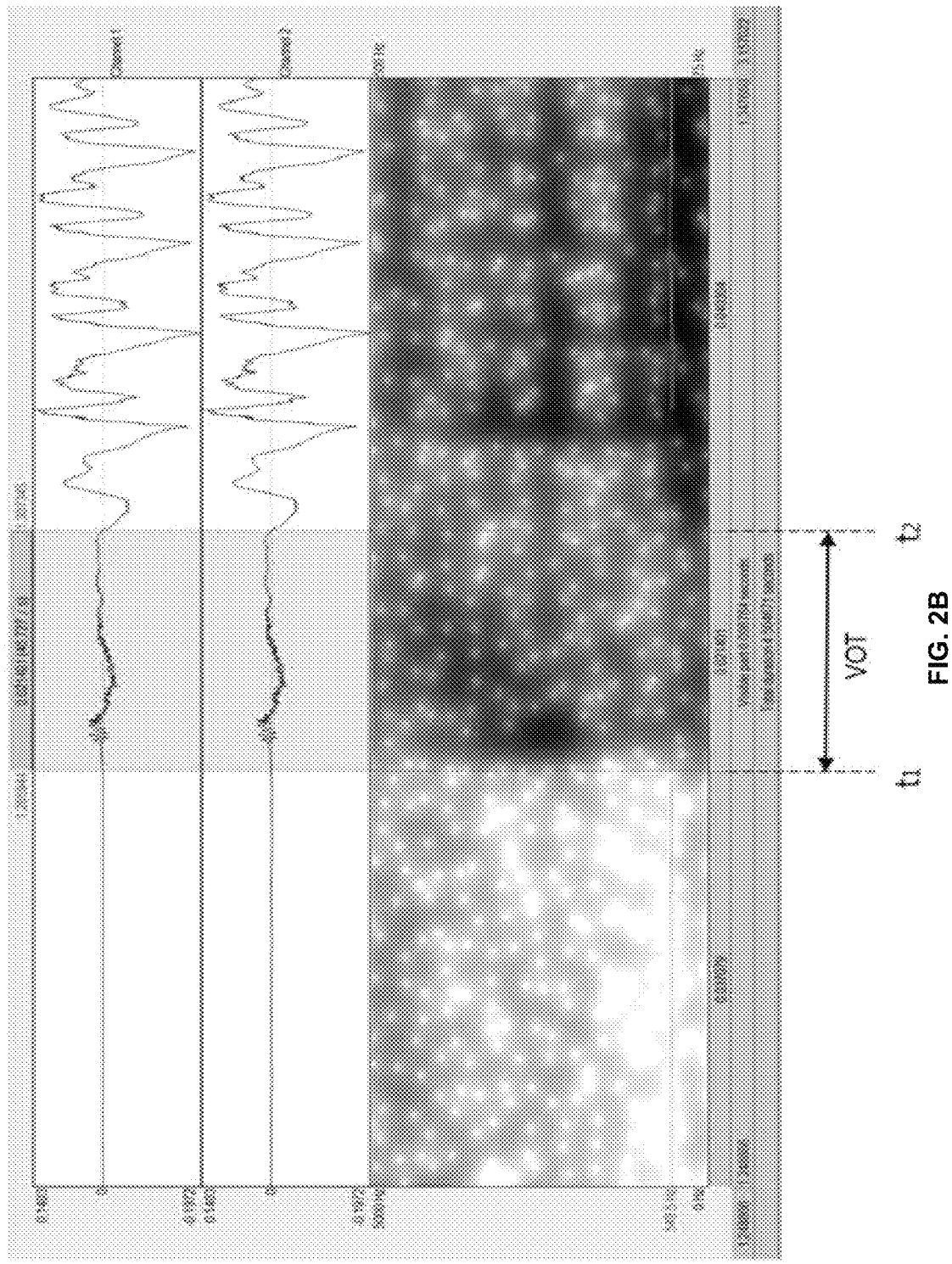

SYSTEM AND METHOD FOR DETERMINING STROKE BASED ON VOICE ANALYSIS

STATEMENT REGARDING GOVERNMENT SUPPORT

The present invention was made with the support of Ministry of Science and ICT of Republic of Korea.

REFERENCE TO RELATED APPLICATIONS

This application claims the priority benefit of Korean Patent Application No. 10-2018-0121650 filed on Oct. 12, 2018, the entire contents of which are incorporated herein by reference.

FIELD OF THE INVENTION

The present invention relates to system and method for determining stroke or apoplexy (cerebrovascular accident) based on voice analysis. More specifically, the present invention relates to the system and method for determining persons having a stroke or with a high probability of having a stroke, by recording the sound of each person in a test group, which is made of a normal group (i.e., people who currently does not have stroke and has no history of stroke) and a stroke patient group (i.e., people who is diagnosed with stroke), reading a predetermined word to prepare voice data, then analyzing the voice onset time (VOT) from the prepared voice data of each person of the test group to identify the specific characteristics that enable identification of a person with a stroke.

BACKGROUND OF THE INVENTION

Not only is stroke the most common cause of death as a single medical symptom, but it is often associated with a high rate of long term, if not permanent, post-stroke disability and complications, resulting in burdensome medical expenses. Countries with a rapid aging population trend such as South Korea, are facing a huge economic problems related to ever increasing medical expenses and insurance costs. Occurrence rate of stroke is particularly high among elderly people, and thus prevention of stroke and appropriate treatment and management remain important issues at the individual and national level.

Stroke has a very high mortality rate, thus many researches are actively conducted to prevent stroke and early recognition of stroke. Most of researches being conducted in various fields to determine the stroke are based on measuring vital signs of a test subject, such as abnormal heart rhythms and arrhythmias.

Although the mortality rate from the onset of stroke is decreasing, increasingly growing number of population are left with serious post-stroke disabilities. Symptoms often include hemiplegia, muscle weakness of the face, numbness, reduction in sensory or vibratory sensation, initial flaccidity (reduced muscle tone), replaced by spasticity (increased muscle tone) or excessive reflexes, which may cause unbalanced posture or other physical dysfunctions. For example, stroke complications include unilateral paralysis, speech disorders, visual disturbances, dizziness, headache, numbness, sensory disturbances, vomiting, speech disturbances, facial paralysis, coma, and swallowing disorders.

Other representative symptom of stroke includes aphasia, dysarthria or other types of language disorders that hinders basic communication skills, resulting in serious difficulties in daily life practice and restriction of personal activities, social activities, and occupation. Disruption in self-identity, relationships with others, and emotional well-being can lead to social consequences after stroke due to the lack of ability to communicate. These language disorders tend to recover naturally, but neurological speech impairment may occur due to partial or complex problems of the nervous system, even if recovery is achieved.

Particularly, in the elderly patients, the physiological change due to aging causes negative characteristics such as drowsy voice, hoarseness, rough voice, squeezing voice, frequent phonation breakdown, and voice trembling, which causes linguistic difficulty. These respiratory and neurological speech disorders and various voice problems in elderly patient group can negatively affect the social function and quality of life of such patients, and speech rehabilitation and neurological approach to speech rehabilitation are urgent.

Dysphagia is a medical term for swallowing difficulties, which may be caused by various abnormalities that can occur on the pathway from oral to gastrointestinal tracts. It is reported that about 40-80% of stroke patients experiences some form of dysphagia, and about one-third of stroke deaths are caused by aspiration pneumonia related to swallowing disorders. Many clinicians consider the change of voice after aspiration to be one of the most common symptoms for identifying dysphagia, with as high as 80% accuracy rate, yet the evaluation method itself is somewhat subjective. A number of previous studies have attempted to come up with more concrete and objective way of demonstrating the linkage between the changes in the voice and the swallowing disorders. Likewise analyzing abnormal speech can be one of the most effective ways to accurately identify stroke in emergency situations and to provide appropriate treatment.

SUMMARY OF THE INVENTION

An object of the present invention is to provide a stroke patient determination method by collecting and analyzing voice data obtained from a plurality of test subjects.

Another object of the present invention is to provide a stroke determination system that uses certain characteristics of voice onset time obtained from the voice data of each of a plurality of test subjects.

In order to achieve the above objects, the stroke determination system of the present disclosure creates the voice data of a test group, which comprises a sub-group of people who is healthy (i.e., normal group) and another sub-group of people who is known to have stroke (i.e., stroke patient group). The sound of each person of the test group reading a predetermined word is recorded, and the voice onset time is obtained from each of the recordings. Then, the start time of the vocal vibration of the collected voice data is extracted and measured, and the stroke patient is identified according to a statistical analysis of the measured voice onset time. The stroke determination system of the present disclosure can determine a stroke patient by using the voice onset time of the voice data.

According to another aspect of the present disclosure, there is provided a stroke determination system comprising: a voice input unit for obtaining a voice input when a predetermined word that includes a plosive sound (consonant) is read by each person of the test group, which is made of a normal group and a stroke patient group; a voice recording unit for generating voice data from the voice input gathered by the voice input unit, and storing the generated voice data; a speech analysis unit for extracting voice onset time (VOT) from each of the voice data stored in the voice recording unit and obtaining one or more probability parameters associated with the VOT; and a stroke determination unit that calculates a first probability of belonging in the normal population and a second probability of belonging in the stroke patient group according to an integration section defined from the parameters obtained by the voice analysis unit, then apply Bayes' theorem to the first probability and the second probability to determine whether an individual is a stroke patient.

In one embodiment, the stroke determination unit is configured to set the integration section based on a minimum value and a maximum value of the probability parameters for the voice onset time of a normal group as well as a minimum value and a maximum value of the probability parameters for the voice onset time of stroke patient group.

In another embodiment, each of the first and second probabilities is obtained by a probability parameter distribution diagram by using the probability parameters, and by obtaining a first integral value associated with the voice onset time of the normal group and a second integral value associated with the voice onset time of the stroke patient group in the integration section.

In another embodiment, the stroke determining unit is configured such that, when the integration section is from 0.02 to 0.024, then 33.7% of the test subjects falling within the integration section to be the stroke patient.

As described above, the stroke determination system of the present disclosure collects voice data of a subject to be measured, extracts and analyzes the voice onset time to perform speech based stroke determination.

In addition, the stroke determination system of the present disclosure uses probability parameters of a normal group and a stroke patient group in applying the Bayesian theorem, which in turn, compared and analyzed to determine a stroke patient.

Further, the stroke determination system of the present invention can accurately determine the prognosis of a patient by determining a stroke patient by statistical analysis of the voice onset time of voice data, which allows for early identification of stroke to initiate preventative treatment methods.

BRIEF DESCRIPTION OF THE DRAWINGS

FIGS. 2A and 2B are waveform diagrams illustrating exemplary a voice onset time of voice data according to an embodiment of the present disclosure.

DETAILED DESCRIPTION OF THE INVENTION

Figure 1:
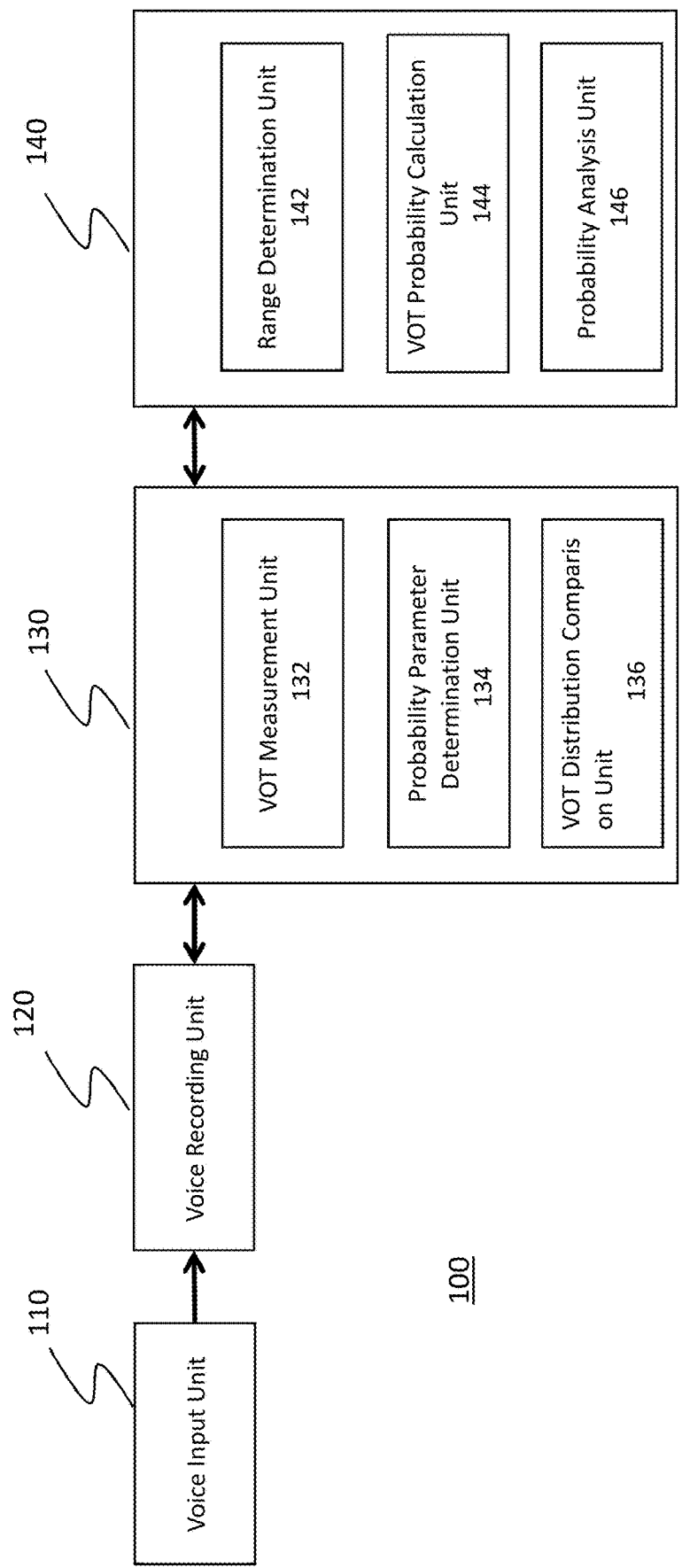
FIG. 1 is a block diagram showing an exemplary stroke determination system using speech analysis of a subject according to an embodiment of the present disclosure.

The embodiments of the present invention can be modified into various forms and the scope of the present invention should not be interpreted as being limited by the embodiments described below. The present embodiments are provided to enable those skilled in the art to more fully understand the present invention. Accordingly, the shapes and the like of the components in the drawings may be exaggerated in order to emphasize a clearer explanation.

Hereinafter, embodiments of the present invention will be described in detail with reference to the accompanying drawings.

Figure 2A:
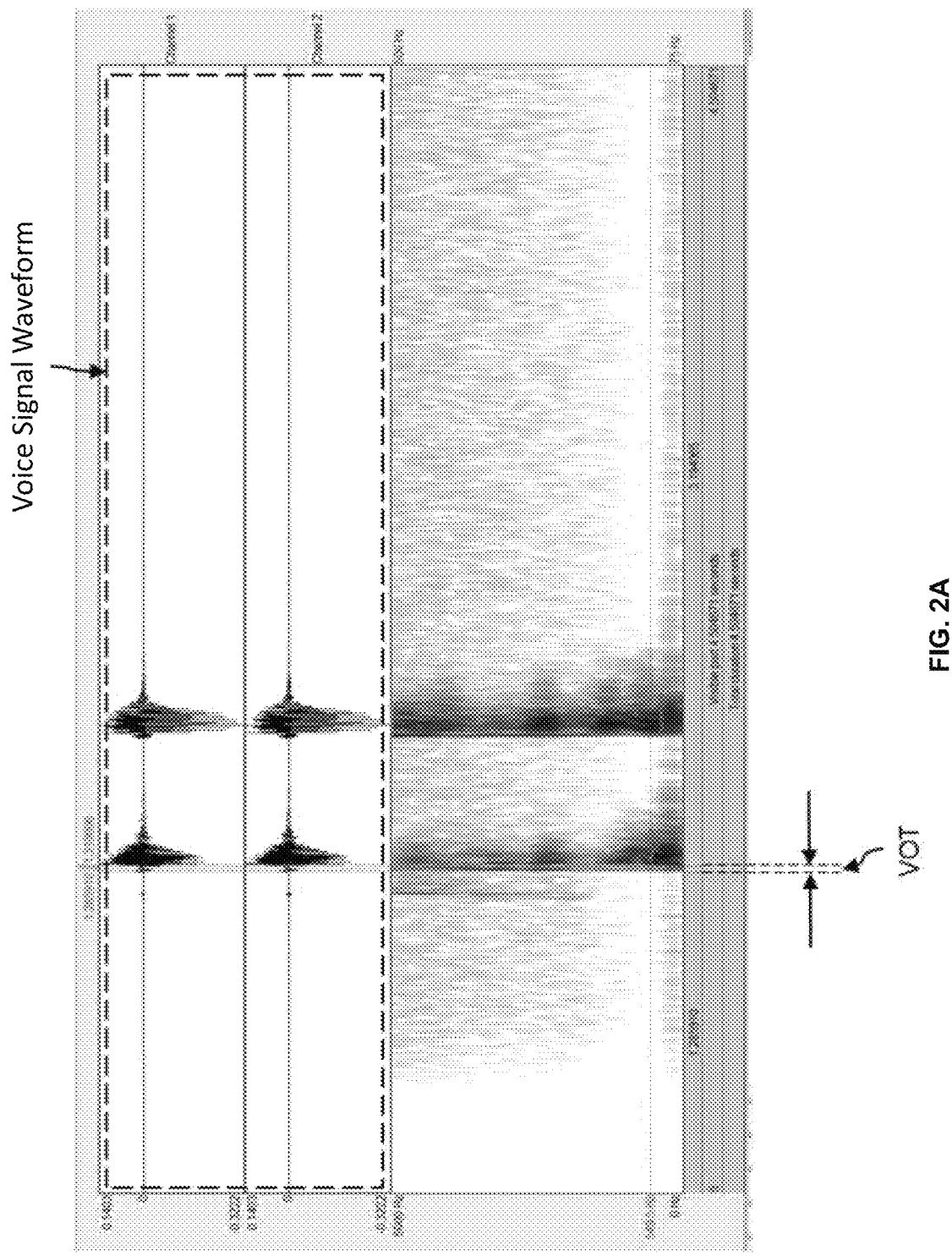
Figure 3:
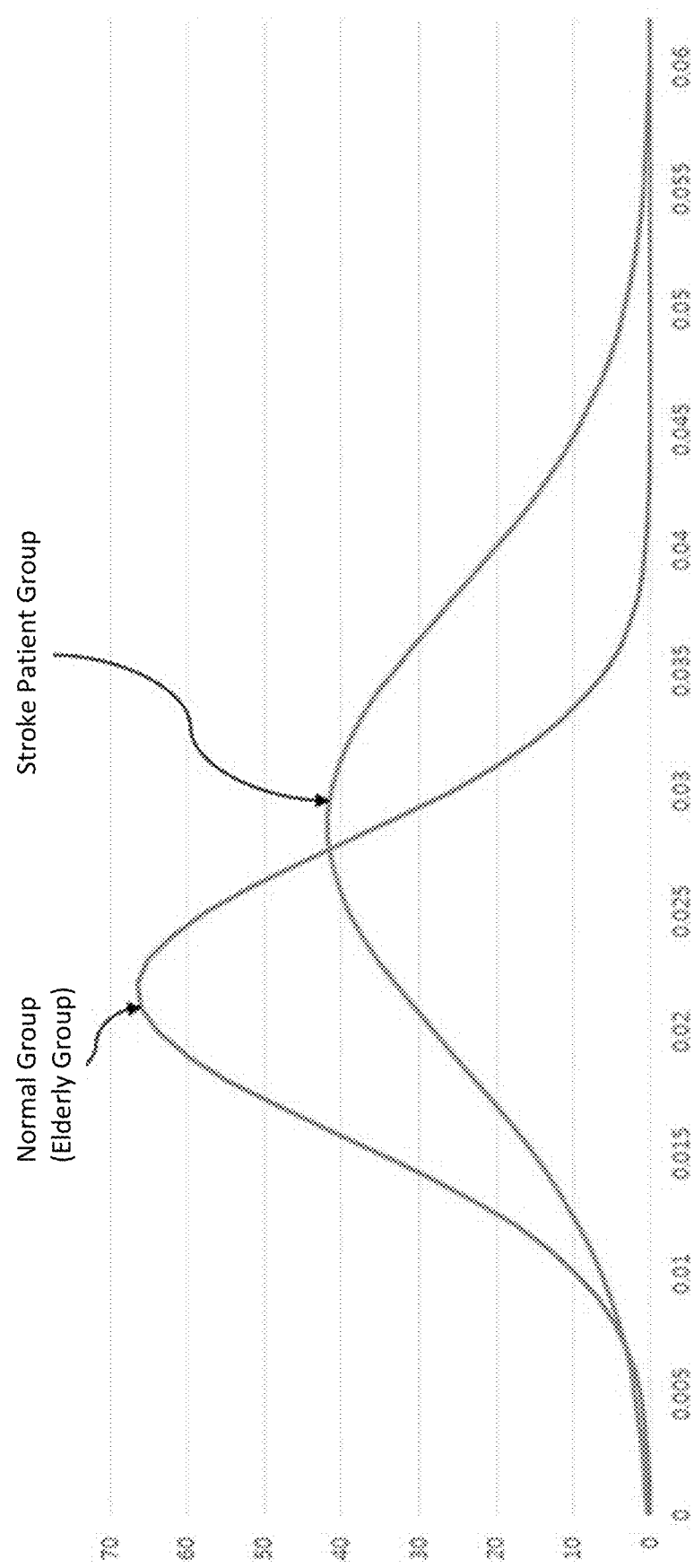
FIG. 3 is a graph illustrating comparison between the probabilistic parameter distribution diagrams of the voice onset time of a normal group and the probabilistic parameter distribution diagrams of the voice onset time of a stroke patient group depicted in FIGS. 2A and 2B.
Figure 4:
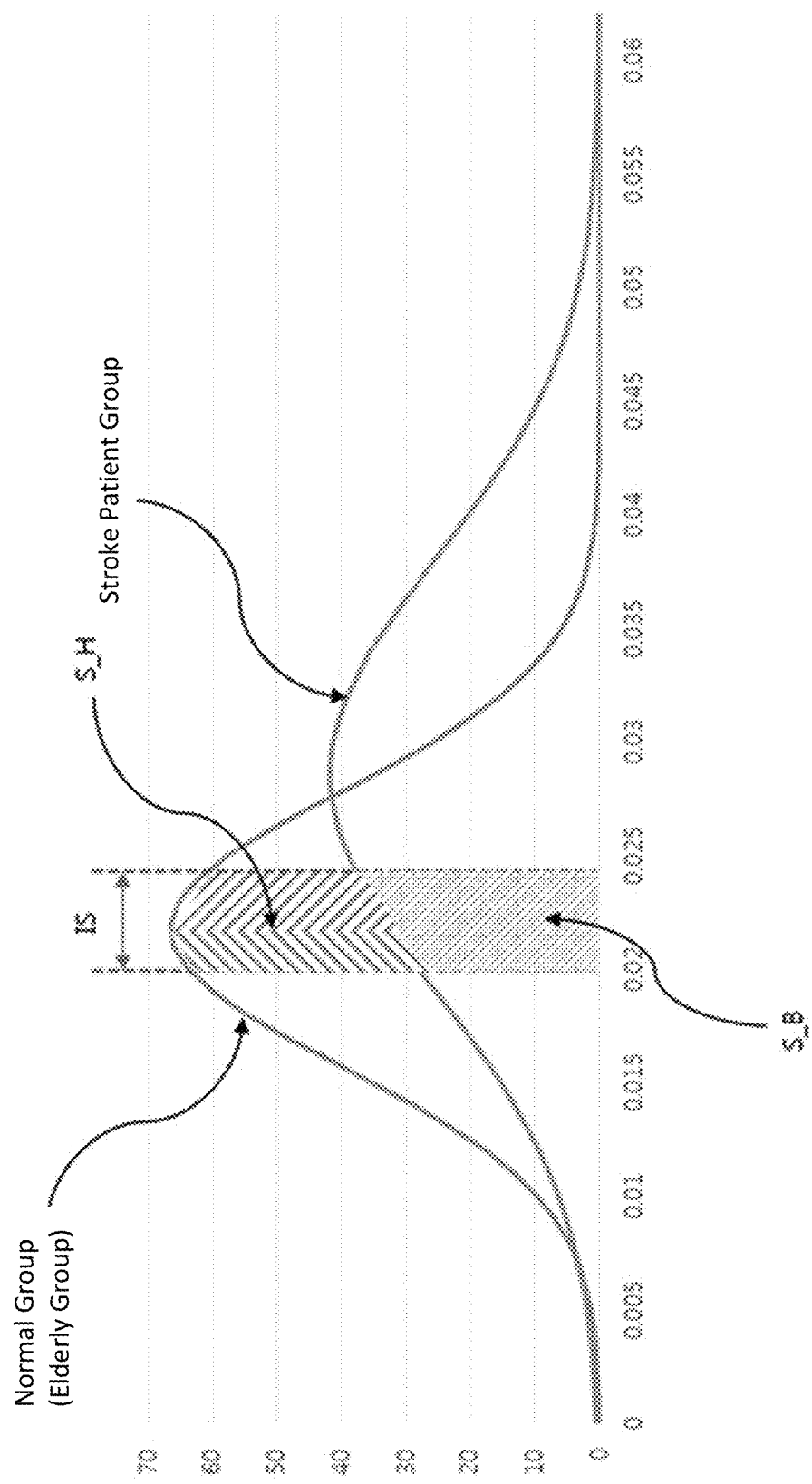
FIG. 4 is a graph illustrating a calculation of a probability of a normal group and a stroke patient group.
Figure 5:
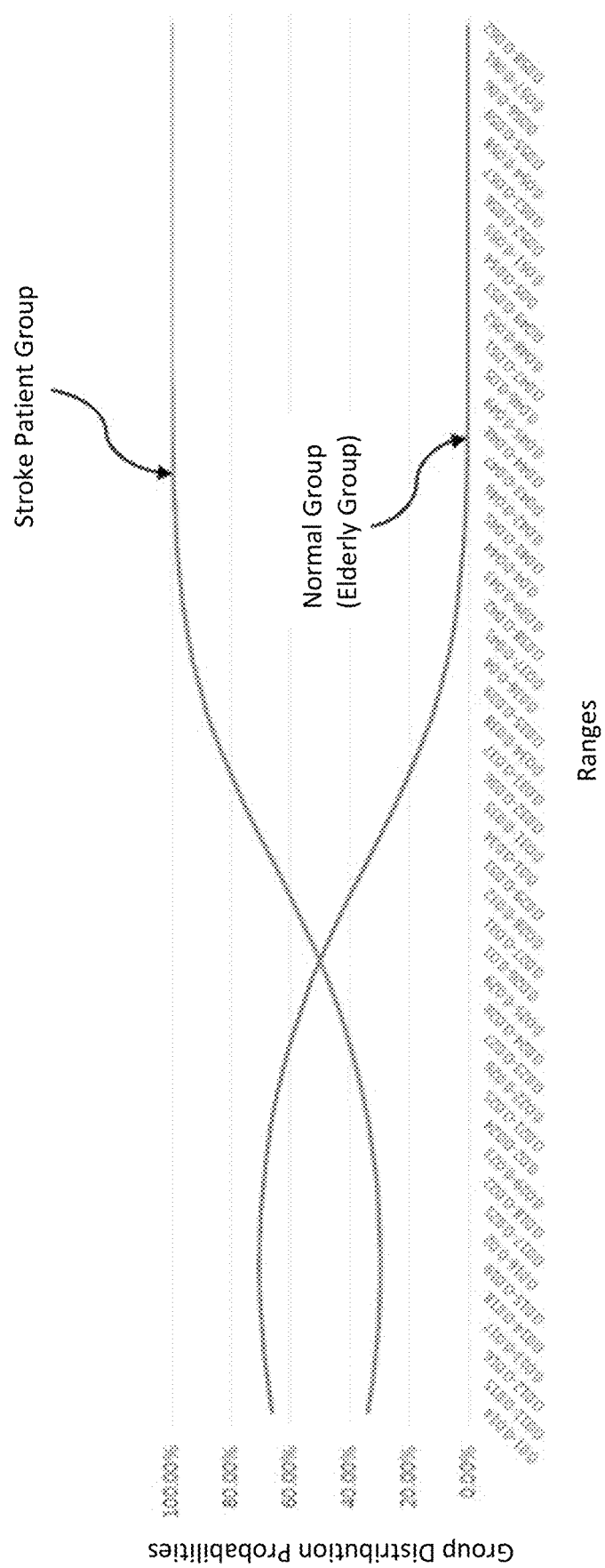
FIG. 5 is a graph showing a population probability distribution diagram to be included in each of the normal group and the stroke patient group.

FIG. 1 is a block diagram showing an exemplary configuration of a speech analysis based stroke determination system. FIGS. 2A and 2B are waveform diagrams showing exemplary voice onset time of voice data. In FIG. 3 illustrates a comparison between the probabilistic parameter distribution diagrams of the voice onset time of a normal group and a stroke patient group of FIGS. 2A and 2B. FIG. 4 is a diagram for calculating a probability of a normal group and a stroke patient group. FIG. 5 is a probability distribution diagram to be included in each of the normal group and the stroke patient group.

Referring to FIGS. 1 to 5, the stroke determination system 100 of the present disclosure determines a stroke patient using voice data collected from each of a plurality of test subjects. To this end, the test subjects read a certain word multiple times under the same environment. The sound of the subjects reading the predetermined word is recorded and collected every time, and characteristics associated with the voice onset time (VOT) of each of the collected voice data are stochastically analyzed to determine whether the test subject has stroke.

Specifically, the stroke determination system 100 includes a voice input unit 110, a voice recording unit 120, a voice analysis unit 130 and a stroke determination unit 140. While it is not specifically depicted in FIG. 1, the stroke determination system 100 may include a network module, which provides a network connection between the stroke determination unit 100 and a network server. For instance, the stroke determination system 100 may be configured to communicate with another stroke determination system or other types of ancillary systems provided at hospitals or other medical research facilities to exchange the voice data or other stroke related speech analysis data to enhance the accuracy of the stroke determination system 100.

The voice input unit 110 is provided with a means for receiving sound input, for example, a microphone, a headset microphone, or the like. In order to minimize the variability of speech, each of the test subjects may be asked to read a specific word under the same environment condition with minimal noises. The voice input unit 110 receives the voice sound and outputs the voice signal to the voice recording unit 120. Here, the predetermined word should be a word containing a plosive sound such as 'straight', 'sea', 'meat', and the test subject should read the word multiple times (for instance, at least three times). Further, the distance between the mouth of the test subject and the voice input unit 110 should remain substantially constant (for example, in the range of about 5 to 15 cm) when the test subject is reading the predetermined word.

The group of test subjects is composed of a normal group and a stroke patient group. In the example provided in the present disclosure, the test group includes 173 elderly people as a normal group and 46 stroke patients as a stroke patient group as shown in Table 1 below. The voice data collected from each of the test subjects in the test group is analyzed to determine whether or not a stroke has occurred.

TABLE 1

|  | Elderly people | Stroke patients |
|---|---|---|
| Number of collected data | 173 | 46 |

Everyone in the test group is able to read the given word. The normal group is composed of individuals who are 65 years old or older with no history of stroke. The stroke patient group is composed of individuals who have a history of stroke on the hospital diagnostic records as of August 2018.

The voice recording unit 120 is a means for recording the sound signal receiving from the voice input unit 110, for example, a voice recorder, a computer device, or the like. The voice recording unit 120 is configured to receive the voice signals output from the voice input unit 110 to generate and store voice data. The voice data may be a digital voice data, which is readable by the voice analysis program provided in the stroke determination system 100, which may be a part of the voice analysis unit 130.

The voice analysis unit 130 may be a voice analyzer, or a computer device provided with a voice analysis program, and the like. The voice analysis unit 130 configured to read the voice data generated by the voice recording unit 120 to process voice analysis. The voice analysis unit 130 may be provided with a voice analysis program capable of monitoring, extracting, editing, and analyzing voice data such as PRAAT, spectrogram, and the like.

According to one embodiment, the voice analysis unit 130 includes a voice onset time (VOT) measurement unit 132 that measures the voice onset time (VOT) of each of the measurement subjects, a probability parameter determination unit 134 for determining probability parameters for each of the measured voice onset time (VOT), and a VOT distribution comparison unit 136 that compares the distribution of probability parameters for the normal group and the stroke patient group to distinguishes between the normal group and the stroke patient group.

Specifically, the VOT measuring unit 132 reads the voice data generated by the voice recording unit 120, and extracts and measures the voice onset time (VOT), which serves as the basis for setting the integration section for determining a stroke patient.

Here, the voice onset time (VOT) is the interval from the moment the closed mouth is opened to the start of the vibration of the vocal cords. In other words, it is the time period from the moment vocal cords are opened by the plosive sound (consonant) of the predetermined word and until the vocal cords start to vibrate for the vowel that follows the plosive sound. As shown in FIGS. 2A and 2B, the voice onset time (VOT) is the portion indicated by red in the voice signal waveform, which is a period from the moment (t1) in which the amplitude starts at 0 to the moment (t2) when the amplitude returns to 0. Accordingly, the section of the voice onset time (VOT) to be measured in the voice signal waveform of FIG. 2A is extracted and enlarged as shown in FIG. 2B, and then the voice onset time (VOT) is measured. In the embodiment shown in FIGS. 2A and 2B, the voice onset time (VOT) is measured in about 0.0214 second.

The probability parameter calculating unit 134 calculates probability parameters for the voice onset time (VOT) measured by the VOT measuring unit 132. The probability parameters include the mean, standard deviation, minimum and maximum values for voice onset time (VOT) of each of the normal group (elderly people) and stroke patient group.

The values of the probability parameters are shown in Table 2 below.

TABLE 2

|  | Group | Mean | Standard Deviation | Minimum | Maximum | T-test Result |
|---|---|---|---|---|---|---|
| Voice Onset Time (VOT) | Elderly people | 0.0217 | 0.0060 | 0.0101 | 0.0413 | P < 0.05 |
|  | Stroke patient | 0.0285 | 0.0096 | 0.0144 | 0.0560 |  |

In table 2, the average of the voice onset time (VOT) of the normal group (elderly group) was 0.0217, the standard deviation was 0.0060, the minimum value was 0.0101, and the maximum value was 0.0413. For stroke patient group, the average of voice onset time (VOT) was 0.0285, the standard deviation was 0.0096, the minimum value was 0.0144, and the maximum value was 0.0560.

Also, the significance p value of the T-test result means, when assuming the null hypothesis, the probability that a value will be far above the sample test amount from the null hypothesis. If this p-value is less than the significance level, the null hypothesis is rejected. However, in this example, the significance level is set to 0.05, and thus there is a meaningful difference if the significance level p in the t-test result is smaller than the significance level. Based on the result of observing the change of the probability parameter with respect to the voice onset time (VOT) through the t-test, the significance (p value) of the two groups was smaller than the significance level (0.05). Accordingly, there was a significant difference between the VOT of the normal group and the VOT of the stroke patient group.

The VOT distribution comparison unit 136 compares the distribution of the normal group and the stroke patient group using the probability parameters of each test subject calculated by the probability parameter calculation unit 134. It also distinguishes characteristics between the normal group and the stroke patients group. It is possible to distinguish the characteristics of the normal group and the stroke patient group because the test group was divided into the normal group and the stroke patient group before the measurement of the voice onset time (VOT).

Using the probability parameters calculated by the voice analyzer 130, the probability parameter distribution for the voice onset time (VOT) of each of the normal group and the stroke patient group can be represented in a normal distribution curve by a probability density function as shown in FIGS. 3 and 4.

Here, the probability density function is as shown in the following equation 1.

$$f(x) = \frac{1}{\sqrt{2\pi\sigma^2}} e^{-\frac{(x-m)^2}{2\sigma^2}} \qquad \text{Equation 1}$$

Here, "x" is a random variable for the voice onset time (VOT) of a normal or stroke patient population, and f (x) is a probability density function for the voice onset time (VOT) of a normal or stroke patient population. "m" represents the mean value of the normal population or the stroke patient population, and σ represents the standard deviation of the normal population or the stroke patient population.

In this way, the voice analysis unit 130 can classify the normal people group and the stroke patient group by comparing the probability parameter distribution diagram.

Then, the stroke determination unit 140 determines the range of the voice onset time (VOT) for stroke determination based on the probability parameters calculated from the voice analysis unit 130. Based on the determined VOT range, the stroke determination unit 140 calculates a probability of a test subject, which, in turn, determines whether the subject is a stroke patient.

In an embodiment, the stroke determination unit 140 includes a range determination unit 142 that determines a range for determining a stroke stochastically in a measurement interval of the voice onset time (VOT). The stroke determination unit 140 may also include a VOT probability calculation unit 144 for calculating a probability of a test subject based on the determined range, and further, a probability analysis unit 146 for determining whether the test subject is a stroke patient based on the calculated probability.

Specifically, the range determination unit 142 determines the range of the VOT measurement interval for determining the stroke patient, that is, the integration section (IS) for the normal distribution group H and the stroke distribution group B. In an embodiment, the range determination unit 142 is configured to measure the VOT of each of the test subjects a plurality of times (e.g., at least three times) to obtain the parameters, then determine the range (IS) for the VOT based on the minimum and maximum values among the those obtained parameters. In the example shown in FIG. 4, the range determination unit 142 has determined the range (IS) for the vocal cords oscillation start time to be 0.02 to 0.024.

The VOT probability calculation unit 144 calculates the probability for the test subject according to the range (IS) of the voice onset time (VOT) that was determined by the range determination unit 142. The probability by the range (IS) of the voice onset time (VOT) can be obtained by calculating the integral value of the corresponding range in the probability density distribution chart of each group.

In this example, which is based on the range 0.02 to 0.024 for the cords vibration start time, the VOT probability calculation unit 144 calculates the probability of the test subjects as integral value 0.323 for the normal group and integral value 0.164 for the stroke patient group.

The probability analysis unit 146 determines a stroke patient by applying the probability of being included in the normal population and the probability of being included in the stroke patient group (which is calculated by the integral value of the VOT range) to the Bayes' theorem.

The Bayes theorem shows the relationship between the prior probability and the posterior probability of two random variables. In the present embodiment, both the prior probability P(B) of the stroke patient group and the prior probability P(H) of the normal group are set to 0.5.

Here, P(B) is a prior probability or marginal probability for event B in a state that has not been affected by event A. P(A|B) is a conditional probability in which event A will occur after the occurrence of event B. It is also called a posterior probability, because P(A|B) depends on specific information about event B. P(B|A) is the conditional probability of event B which depends on event A. P(B) is the prior probability or marginal probability for event B. P(B) serves to normalize the probability of P(A|B).

Specifically, the probability analysis unit 146 calculates a probability of belonging to the normal group P(H|I) within the range of the voice onset time (VOT) through the following equation 2.

$$P(H \mid I) = \frac{P(I \mid H)P(H)}{P(I)} = \frac{P(I \mid H)P(H)}{P(I \mid H)P(H) + P(I \mid B)P(B)} \qquad \text{Equation 2}$$

Here, "H" denotes a normal group among the test group, "B" denotes a stroke patient group among the test group, and "I" denotes interval data indicating a range of the voice onset time (VOT). Thus, P(H) is the probability of belonging to the normal population, and P(B) is the probability of belonging to the stroke patient population. P(I) is the probability that the range of the voice onset time belongs.

P(I|H) is the integral value of the normal population in the measurement interval data (I) of the voice onset time. P(I|B) is the integration value for the stroke patient population in the measurement interval data (I) of the voice onset time.

Accordingly, the probability analysis unit 146 calculates the probability P(H|I) belonging to the normal population in the integration section. The probability analysis unit 146 may calculate the probability P(B|I) belonging to the stroke patient group in the integration section through the following equation 3.

$$P(B|I)=1-P(H|I) \qquad \text{Equation 3}$$

In the example shown in FIG. 4, the integration section (IS) is determined in a range between 0.02 and 0.024. Within the integration section (IS) range of 0.02 to 0.024, the integrated value (S_H) for the normal population is 0.323 and the integrated value (S_B) for the stroke patient population is 0.164. Applying the Bayesian theorem, the probability of a normal person group is 66.3%, and the probability of belonging to a stroke patient group is 33.7%.

In other words, for a test subject exhibiting the voice onset time (VOT) between 0.02 and 0.024, the stroke determination unit 140 will determine the probability of that subject having a stroke is 33.7%. Therefore, in the embodiment of the present invention, when the voice onset time of the subject is within the range of 0.02 to 0.024, 33.7% of the subjects to be measured at that position are judged to be stroke patients.

The result of the determination can be represented by the population distribution probability as depicted in FIG. 5. This population distribution probability represents the probability of being included in the normal population and the stroke patient group when the difference between the minimum value and the maximum value is 0.004, and the range is gradually changed by +0.004 from 0.01.

Specifically, the population distribution probability represents a probability change for each range from 0.01 by adding +0.004 thereto. This is because the difference between the minimum value and the maximum value is usually 0.004 in three measurements. As such, each range 0.01 to 0.014, 0.011 to 0.015, 0.012 to 0.016, which is obtained by adding 0.004, represents the probability distribution to be included in each group.

Figure 6:
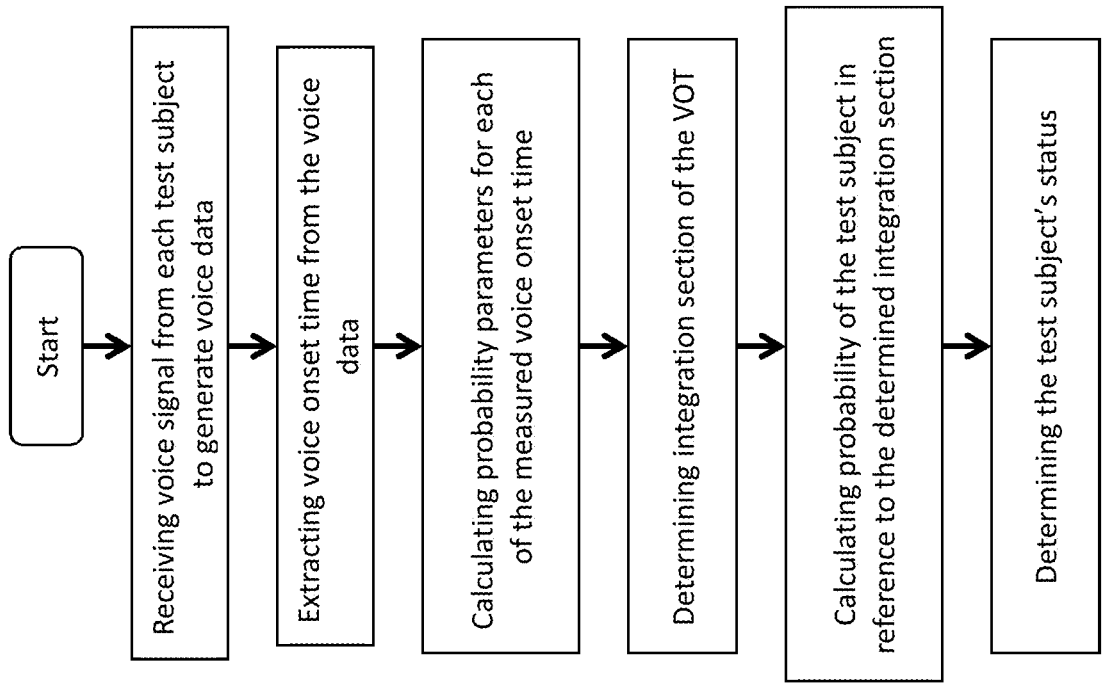
FIG. 6 is a flowchart illustrating a stroke determination procedure using voice analysis of a test subject according to an embodiment of present disclosure.

FIG. 6 is a flowchart illustrating a process of determining stroke based on speech analysis according to the present invention. This process may be performed by the exemplary stroke determination system 100 shown in FIG. 1, which includes the speech input unit 110, the voice recording unit 120, the voice analysis unit 130, and the stroke determination unit 140.

Referring to FIG. 6, in step S200, a voice signal from each of a test subject from the group of test subject is recorded. The group of test subjects is composed of a normal group and a stroke patient group. The voice signal is the sound of the test subject reading a predetermined word that includes plosive sound. The voice signal from each test subject is obtained multiple times (for example, three times). Also, the voice signal from all test subjects should be obtained under the same environment. As described above, the voice signal from each of a plurality of test subjects may be received through the voice input unit 110, and transmitted to the voice recording unit 120 for further generation of voice data from the corresponding to the voice signal.

In step S210, the voice onset time (VOT) is extracted from the voice data. As described above, extraction of the voice onset time (VOT) from the voice data may be performed by the voice analysis unit 130.

In step S220, probability parameters for each of the measured voice onset time (VOT) are calculated. The probability parameters include the mean, standard deviation, minimum value, and maximum value of the voice onset time (VOT) of each of the normal group and the stroke group. The probability parameters may be calculated by the voice analysis unit 130. The voice analysis unit 130 may further be configured to compare the distribution of the normal population with the stroke patient group using the calculated probability parameters, thereby distinguishing the normal people group from the stroke patient group.

In step S230, the integration section of the VOT of each of the distribution charts of the normal population and the distribution of the stroke patient group is determined. The integration section is determined based on the minimum value and the maximum value among the calculated probability parameters obtained by measuring the voice onset time (VOT) of each of the subjects. Here, the integration section of the VOT may be determined by the stroke determination unit 140 determines the range of the voice onset time (VOT) for stroke determination using the probability parameters of the voice onset time (VOT) calculated by the voice analysis unit 130. In the example depicted in FIG. 4, the integration section is determined to be 0.02 to 0.024.

In step S240, the probability of the test subject is calculated based on the subject's VOT in reference to the determined integration section from the test group. At this time, the probability of the integration section IS of the voice onset time (VOT) can be obtained by calculating the integrated value for the integration section in the probability density distribution chart of each group. In the example shown in FIG. 4, the probability of the test subject to be measured by the range integration section 0.02 to 0.024 for the voice onset time (VOT) is calculated to be 0.323 for the normal group and 0.164 for the stroke patient group. As described above, the probability of the test subject may be calculated by the stroke determination unit 140.

Then, in step S250, a test subject's status is determined by applying the probability of being included in the normal group and the probability of being included in the stroke patient group, both of which are calculated by the integration value, to the Bayes theorem of Equation 2. In the example described above, the integrated value for the normal group is 0.323 and the integrated value for the stroke patient group is 0.164 when the range of 0.02 to 0.024 in the integration section. When applying the set of probabilities to the Bayesian theorem, the probability of being included in a normal group is 66.3%, and the probability of belonging to a stroke patient group is 33.7%. In other words, the probability that the test subject having a stroke is 33.7% when the voice onset time (VOT) is between 0.02 and 0.024.

Although the structure and operation of the stroke determination system based on the speech analysis according to the present invention have been described in detail and with reference to the drawings, it is only described by way of example. It will be understood by those skilled in the art that various changes and modifications may be made without departing from the spirit of the invention.

What is claimed is:

1. A stroke determination system comprising:
   a microphone for receiving analog voice signal of a test subject reading a predetermined word, the predetermined word including a plosive sound;
   an analog voice signal to digital voice data converter for generating digital voice data from the analog voice signal obtained by the microphone;
   a computer device provided with a voice analysis program and a stroke determining program, wherein the voice analysis program is configured to extract a voice onset time from the digital voice data and identify probability parameters associated with the extracted voice onset time of the test subject, and wherein the stroke determining program is configured to determine an integration section using the probability parameters identified from the voice analysis program, calculate a first probability of being in a normal group and a second probability of being in a stroke patient group based on the determined integration section, and calculate a probability of the test subject being a stroke patient by applying the first probability and second probability to Bayesian theorem.

2. The stroke determination system according to claim 1, wherein the stroke determining program determines the integration section based on a minimum value and a maximum value of the probability parameters for the voice onset time of each of the normal group and the stroke patient group.

3. The stroke determination system of claim 2, wherein each of the first and second probabilities is calculated by generating a probability parameter distribution diagram using the probability parameters, and calculating a first integral value for the voice onset time of the normal group and a second integral value for the voice onset time of the stroke patient group at the integration section.

4. The stroke determination system according to claim 2, wherein 33.7% of the test subjects are determined to be stroke patients when the integration section is within the range of 0.02 to 0.024.

5. The stroke determination system according to claim 1, further comprising a network module for exchanging the digital voice data, a voice onset time from the digital voice data and the probability parameters associated with the extracted voice onset time with other stroke determination system connected via network to enhance the accuracy in determining the probability of the test subject having a stroke.

6. A method of determining a probability of having a stroke, comprising:
- recording analog voice signal of each of a reference subject of a reference group reading a predetermined word with plosive sound, said reference group consisting of a normal group and a stroke patient group;
- converting each of the analog voice signals recorded from the reference subjects into a corresponding digital voice data;
- extracting a voice onset time (VOT) from each of the converted digital voice data;
- calculating probability parameters for each of the voice onset time (VOT), said probability parameters including a mean, a standard deviation, a minimum value and a maximum value of the voice onset time (VOT) of each of the normal group and the stroke patient group;
- determining an integration section of the voice onset time (VOT) of a probability density distribution chart of the normal group and a probability density distribution chart of the stroke patient group, wherein the integration section determined based on the minimum value and the maximum value among the calculated probability parameters obtained by measuring the voice onset time (VOT) of each of the reference subject within the respective groups;
- recording analog voice signal of a test subject and converting the analog voice signal of the test subject into digital voice data;
- obtaining a probability of the integration section of the voice onset time (VOT) for the test subject by calculating an integrated value for the integration section in the probability density distribution chart of each of the normal group and the stroke patient group; and
- applying the probability of being included in the normal group and the probability of being included in the stroke patient group, both of which are calculated by the integration value, to the Bayesian theorem to determine a probability of the test subject having a stroke.

* * * * *